United States Patent [19]
Teirstein

[11] Patent Number: 5,540,659
[45] Date of Patent: Jul. 30, 1996

[54] IRRADIATION CATHETER AND METHOD OF USE

[76] Inventor: Paul S. Teirstein, 402 Coast Blvd., South, La Jolla, Calif. 92037

[21] Appl. No.: 298,053

[22] Filed: Aug. 30, 1994

Related U.S. Application Data

[63] Continuation-in-part of Ser. No. 231,423, Apr. 22, 1994, Pat. No. 5,472,425, which is a continuation-in-part of Ser. No. 197,970, Feb. 17, 1994, Pat. No. 5,468,225, which is a continuation of Ser. No. 92,332, Jul. 15, 1993, Pat. No. 5,336,184.

[51] Int. Cl.⁶ .................................................. A61M 29/00
[52] U.S. Cl. .......................... 604/104; 604/53; 604/96; 606/194; 600/3
[58] Field of Search .................. 604/52–53, 96–105; 606/192, 194, 2, 7, 13, 14, 27, 32–34; 600/3, 7

[56] References Cited

U.S. PATENT DOCUMENTS

| | | | |
|---|---|---|---|
| 4,183,102 | 1/1980 | Guiset | 604/101 |
| 4,762,129 | 8/1988 | Bonzel . | |
| 4,771,777 | 9/1988 | Horzewski et al. . | |
| 4,819,751 | 4/1989 | Shimada et al. . | |
| 4,909,781 | 3/1990 | Husted . | |
| 4,944,745 | 7/1990 | Sogard et al. . | |
| 5,040,548 | 8/1991 | Yock . | |
| 5,053,033 | 10/1991 | Clarke | 606/7 |
| 5,061,273 | 10/1991 | Yock . | |
| 5,106,360 | 4/1992 | Ishiwara et al. | 600/3 |
| 5,135,535 | 8/1992 | Kramer . | |
| 5,147,377 | 9/1992 | Sahota . | |
| 5,154,725 | 10/1992 | Leopold . | |
| 5,156,594 | 10/1992 | Keith . | |
| 5,171,222 | 12/1992 | Euteneuer et al. . | |
| 5,180,367 | 1/1993 | Kontos et al. . | |
| 5,199,939 | 4/1993 | Dake et al. . | |
| 5,205,822 | 4/1993 | Johnson et al. . | |
| 5,226,888 | 7/1993 | Arney | 604/53 |
| 5,232,445 | 8/1993 | Bonzel . | |
| 5,246,437 | 9/1993 | Abela | 606/13 |
| 5,302,168 | 4/1994 | Hess | 600/3 |
| 5,324,269 | 6/1994 | Miraki . | |
| 5,368,567 | 11/1994 | Lee | 604/102 |
| 5,456,680 | 10/1995 | Taylor et al. | 606/7 |

FOREIGN PATENT DOCUMENTS

| | | | |
|---|---|---|---|
| 4003458 | 8/1991 | Germany | 600/3 |
| WO92/17236 | 10/1992 | WIPO . | |

*Primary Examiner*—John D. Yasko
*Assistant Examiner*—Ronald K. Stright, Jr.
*Attorney, Agent, or Firm*—Gerald W. Spinks

[57] ABSTRACT

A catheter for use with a radioactive source within the catheter to irradiate a selected area of a blood vessel in combination with angioplasty procedures, to prevent restenosis of that area of the blood vessel. The catheter has a guidewire channel formed near its distal end to facilitate use of the catheter as a rapid exchange catheter, allowing insertion of the catheter over a guidewire also used in performance of an angioplasty procedure. The catheter can also have a guidewire channel formed near its proximal end to provide an O-ring sealing surface and to facilitate free guidewire movement. The catheter also has a closed end to retain the radioactive source within the catheter. The catheter can also be provided with a centering balloon or a set of centering wire loops to center the radioactive source radially within the blood vessel.

20 Claims, 4 Drawing Sheets

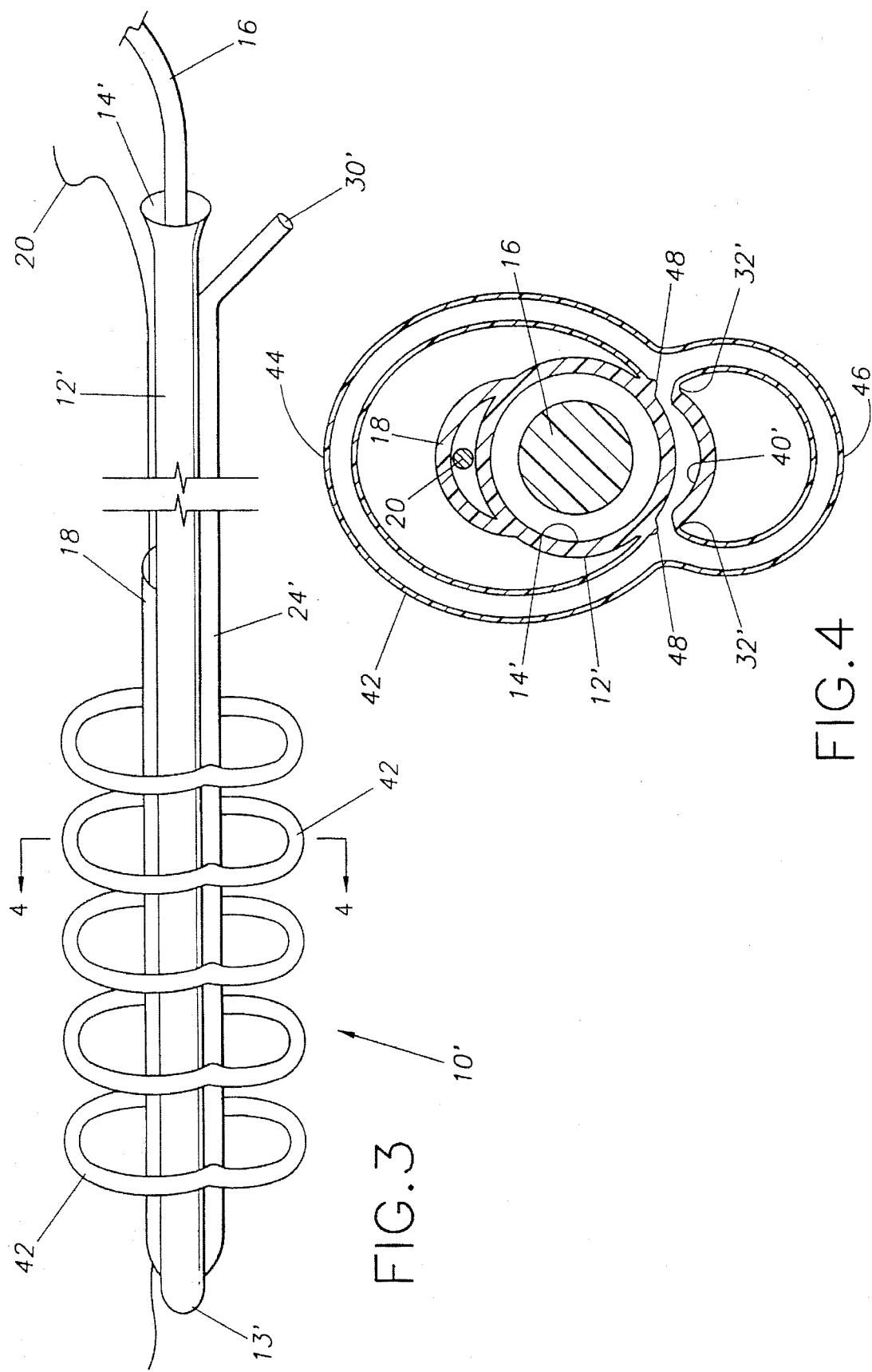

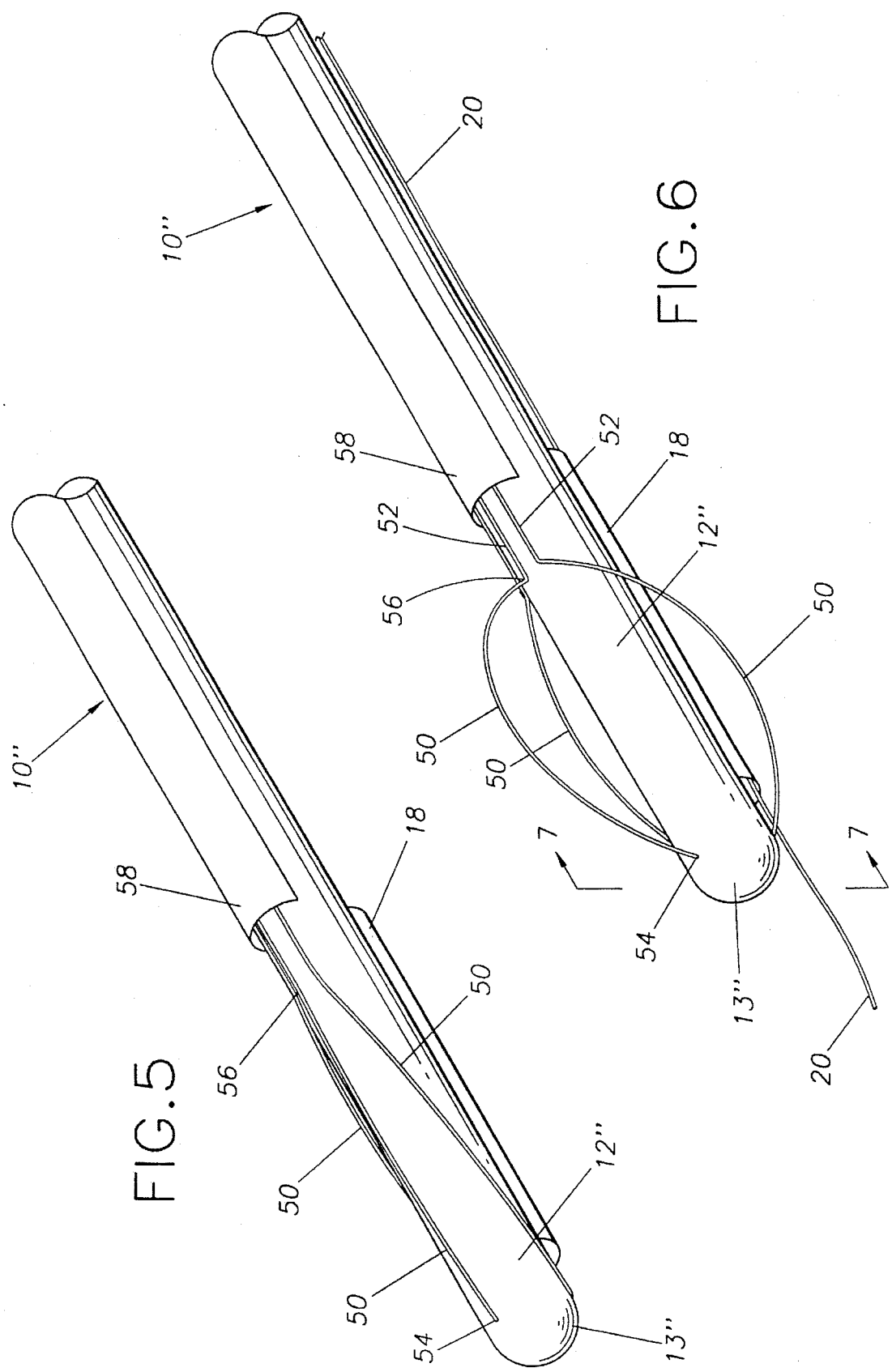

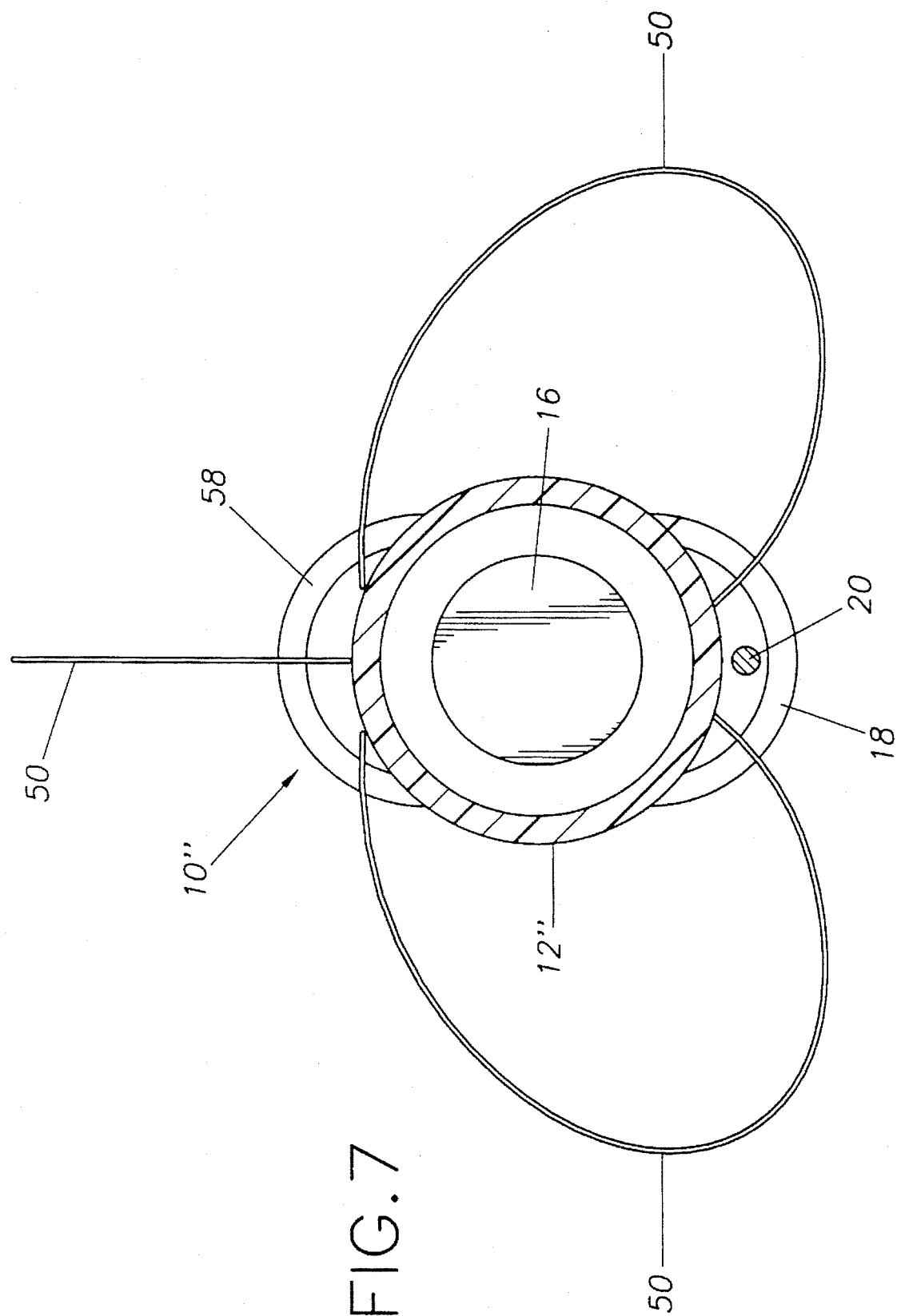

IRRADIATION CATHETER AND METHOD OF USE

RELATED APPLICATIONS

This application is a continuation-in-part of U.S. patent application Ser. No. 231,423, filed Apr. 22, 1994, now U.S. Pat. No. 5,472,425, which is a continuation-in-part of U.S. patent application Ser. No. 197,970, filed Feb. 17, 1994, now U.S. Pat. No. 5,468,225, which is a continuation of U.S. patent application Ser. No. 092,332, filed Jul. 15, 1993, now U.S. Pat. No. 5,336,184.

FIELD OF INVENTION

The present invention is in the field of devices used to subject portions of a blood vessel to nuclear radiation to prevent restenosis of the irradiated area after performance of an angioplasty procedure.

BACKGROUND OF THE INVENTION

A common problem after performance of a percutaneous transluminal coronary angioplasty is the restenosis of the treated area. In fact, restenosis occurs in 30% to 50% of cases. Restenosis occurs, at least in part, as a result of vascular smooth muscle cell migration, proliferation, and neointima formation at the site of the angioplasty. It has been shown that intracoronary delivery of ionizing radiation causes focal medial fibrosis, which when delivered at the site of the angioplasty, impedes the restenosis process. Adjacent coronary segments and the surrounding myocardium are undamaged by the irradiation treatment.

Delivery of the ionizing radiation at the site of the stenosis can be achieved by the introduction of an irradiation ribbon through an infusion catheter. In known systems, the infusion catheter is inserted to the site of the stenosis over a guidewire which may be inserted before, or left after, the performance of an angioplasty procedure. After insertion of the infusion catheter, the guidewire is removed, and the irradiation ribbon is inserted in its place. The irradiation ribbon typically incorporates a plurality of Iridium-192 seeds or pellets near its distal end. Other sources of ionizing radiation can be used, as well. This plurality of radioactive sources arranged essentially in a line approximates a line source, although the intensity of the radiation will vary axially to some extent, depending upon the spacing and length of the seeds. The irradiation ribbon is inserted to the point where the radioactive material is placed in the area of the stenosis. The Iridium-192 emits gamma radiation having a range of energies between 296 and 612 thousand electron volts (keV).

The currently known systems have several disadvantages. First, the guidewire must be withdrawn before insertion of the irradiation ribbon. Withdrawal of the guidewire is not favored by physicians because it adds at least one step to the procedure, and because it takes additional time. The performance of any additional step presents additional opportunities for complications. Time is of the essence during angioplasty because much of the procedure involves at least partial blockage of the flow of blood in the blood vessel, which can be harmful to the muscle served by the vessel. This problem is compounded during the irradiation procedure, since the radioactive source must often be left in place for several minutes in order to deliver the desired dose of radiation to the vascular tissue. The time problem can be further compounded by the need to reinsert the guidewire after delivering the radiation, in some cases.

A second disadvantage of known systems is that the irradiation ribbon is exposed to blood flow in the infusion catheter, and it is even possible that some of the radioactive seeds could be lost out the distal end of the infusion catheter, or the irradiation ribbon itself can break.

A third disadvantage is that location of the radioactive material radially within the blood vessel is largely uncontrolled. Rotation of the infusion catheter may assist in centering the radiation source within the stenosis, in some cases, but this method is not always effective. Centering of the radioactive material within the tissues injured by the angioplasty may be required, because it is important to deliver a known dose of radiation uniformly to the affected tissue. The intensity of gamma radiation emanating from a line source varies inversely with the square of the radial distance from the source. Therefore, if the radiation source is not centered within the blood vessel, the dose delivered to one side of the vessel can vary greatly from the dose delivered to the opposite side. In addition, if the line source lies at an angle to the centerline of the vessel, rather than being concentric therewith, or at least parallel thereto, the dose delivered can vary axially by an appreciable amount, throughout the length of the stenosis. In some cases, it can even be desirable to position the radiation source parallel to, but offset from, the centerline of the blood vessel, if it is desired to irradiate one side of the stenosis more than the other side. This can be desirable if restenosis is expected to result more from proliferation of the tissues on one side than on the far side.

It is an object of the present invention to provide a catheter assembly for irradiation of a stenotic segment of a blood vessel, which can be inserted to the site of the stenosis over a guidewire. It is a further object of the present invention to provide a catheter assembly which can place an irradiation source at a desired location within a blood vessel, both axially and radially. It is a yet further object of the present invention to provide an irradiation catheter assembly which is economical to manufacture and easy to use.

SUMMARY OF THE INVENTION

A summary of the preferred embodiment of the present invention follows for exemplary purposes. The present invention provides a catheter for use with an irradiation ribbon, with the catheter being constructed to be inserted over a guidewire in place in the blood vessel. The catheter body has an inner lumen into which the irradiation ribbon is inserted. The inner lumen can be sealed at the distal end of the catheter body to fully retain the irradiation ribbon and its incorporated radioactive material.

A guidewire channel is formed on the catheter body, separate from the inner lumen, with at least a portion of the guidewire channel being formed near the distal end of the catheter body. The guidewire channel can be formed having only a short segment at the distal end, allowing the use of the catheter as a rapid exchange catheter, as described in the patent applications cited earlier, upon which this application relies for priority. Alternatively, the guidewire channel can be formed in two separate portions, with one portion near the distal end and one portion near the proximal end of the catheter body. The proximal portion provides a structure surrounding the guidewire, to allow sealing by a guide catheter O-ring while also allowing free guidewire movement. Still further, the guidewire channel can be formed with a lengthwise rupturable membrane. This essentially provides a distal portion for rapid exchange purposes, and a proximal portion for sealing purposes. Both of these latter two embodiments are fully described in the aforementioned applications. Either of these latter embodiments allows the catheter to be used through a guide catheter, providing a proximal fluid tight sealing surface against which the guide catheter O-ring can seal to allow injection of dye to aid in visualization of the radiation source, while simultaneously allowing free guidewire movement which can help position the catheter, as will be discussed below.

Since it may be desirable to position the radiation source radially within the blood vessel, the present invention provides at least two methods, as well as several types of apparatus, for accomplishing the radial positioning. A first method can be employed without any special apparatus, by introducing one or more bends in the guidewire, near its distal end. When the catheter and the irradiation ribbon are axially in place in the area of the stenosis, if the distal end of the catheter is not radially positioned as desired, the guidewire can be rotated to orient the bent portion of the guidewire in the direction in which it is desired to displace the catheter. Then, the guidewire can be slightly withdrawn, pulling one or more bends back into the distal end of the guidewire channel. The bend in the guidewire can cause the guidewire to exert a force against the wall of the guidewire channel, resulting in the desired flexing of the catheter body in the direction of the force, placing the distal end of the catheter in the desired radial location.

To implement an alternative method, the catheter may also be provided with a means for positioning the radiation source radially within the blood vessel. Most often, this positioning means will be used to center the radiation source radially. The positioning means can have various configurations, two examples of which are inflatable balloons and expandable wire loops. An inflatable balloon can be formed as a coil, or as a plurality of essentially annular balloons. The balloon or balloons can be connected to an inflation lumen formed on the catheter body, for inflation purposes.

Alternatively, a plurality of flexible wire loops can be mounted near the distal end of the catheter body, with one end of each loop fixedly attached to the catheter body, and one end free. The wire loops can be shaped to be self expanding when released, or the free end of each loop can be attached to an expansion means which is movable longitudinally by the user to move the free ends of the wire loops toward the attached ends. This movement causes the loops to expand outwardly. The loops can be mounted at spaced intervals about the periphery of the catheter body, to center the catheter within the blood vessel upon expansion. The expansion means can be relatively stiff wires designed to push on proximally located free ends of the wire loops, or they can be wires designed to pull on distally located free ends of the wire loops. Self expanding wire loops would expand without the aid of such expansion means, upon withdrawal of a retaining sheath.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 3 is a perspective view of a second embodiment of the irradiation catheter of the present invention;

FIG. 4 is a sectional view of the catheter shown in FIG. 3, taken at the line 4—4;

FIG. 5 is a perspective view of a third embodiment of the irradiation catheter of the present invention;

FIG. 6 is a perspective view of the catheter shown in FIG. 5, with the wire loops in the expanded position; and FIG. 7 is a sectional view of the catheter shown in FIG. 6.

DESCRIPTION OF PREFERRED EMBODIMENTS

Figure 1:
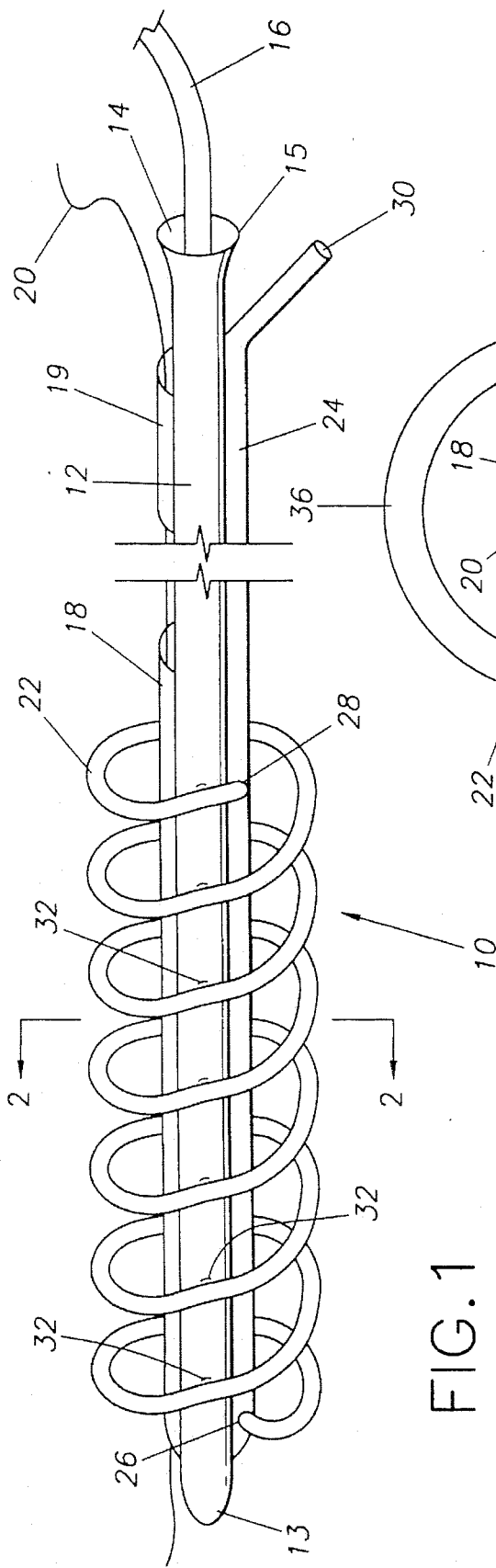
FIG. 1 is a perspective view of a first embodiment of the irradiation catheter of the present invention.
Figure 2:
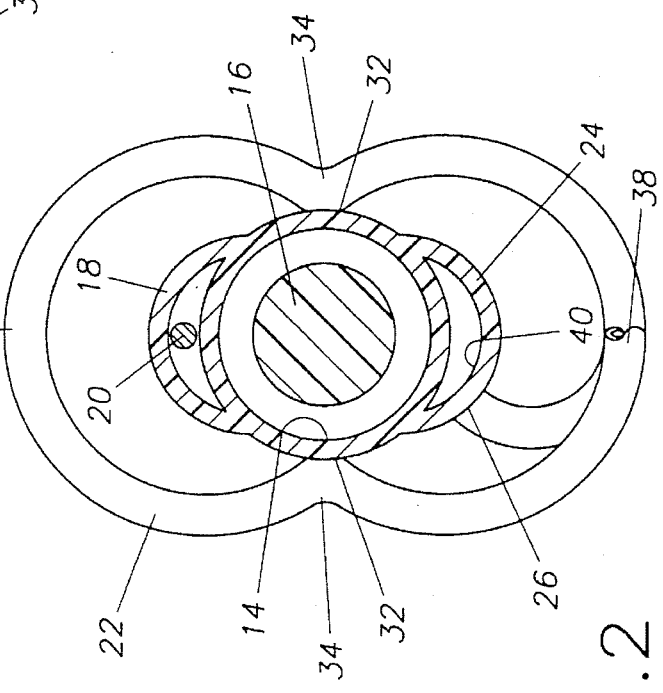
FIG. 2 is a sectional view of the catheter shown in FIG. 1, taken at the line 2—2.

As seen in FIGS. 1 and 2, a first embodiment of the irradiation catheter assembly 10 of the present invention consists generally of a catheter body 12 having an inner lumen 14 which is closed at a distal end 13, an irradiation ribbon 16 insertable within the inner lumen 14, a distal guidewire channel 18 for guiding the catheter body 12 along a guidewire 20, a proximal guidewire channel 19 for sealing against a guide catheter O-ring, a coil shaped centering balloon 22, and an inflation lumen 24 to which the centering balloon 22 is attached. Several of these elements can have different forms in other embodiments, as will be explained, without departing from the spirit of the present invention.

The catheter body 12 is an elongated, hollow, flexible, tubular catheter preferably constructed of a plastic material. The proximal end 15 of the catheter body 12 has a flared end to facilitate insertion of an irradiation ribbon 16 into the inner lumen 14. The irradiation ribbon 16 can be sized to essentially fill the inner lumen 14 to position the irradiation sources concentrically with the catheter body 12. The distal end 13 of the catheter body 12 is closed to retain the irradiation ribbon 16 and its radioactive material.

A guidewire channel 18 is formed on the catheter body 12 separately from the inner lumen 14. The guidewire channel 18 can be formed as a duct affixed to the wall of the catheter body 12 as shown, or it can be formed inside the inner lumen 14, or it can be formed as a lumen passing within a thick catheter wall. The guidewire channel portion 18 shown is formed only near the distal end of the catheter body 12, facilitating the use of the catheter body 12 as a rapid exchange catheter by inserting the proximal end of an in-place guidewire 20 through the guidewire channel portion 18, followed by insertion of the catheter body 12 into the patient over the in-place guidewire 20.

Optionally, a second guidewire channel portion 19 essentially like the distal guidewire channel portion 18 can be formed on the catheter body 12 near its proximal end 15 to provide a sealing surface for a guide catheter O-ring (not shown) if dye injection is to be used. Sealing against the O-ring is achieved without restricting guidewire movement. The proximal guidewire channel portion 19 is placed so that its distal end is closer to the distal end 13 of the catheter body 12 than the length of the guide catheter being used. This insures that, when the distal end 13 of the catheter body 12 reaches the distal end of the guide catheter, the guide catheter O-ring encircles the proximal guidewire channel 19.

A similar advantage can be achieved by making the guidewire channel 18 run the full length of the catheter body 12, with a lengthwise rupturable membrane formed in the wall of the channel (not shown). This essentially provides a distal guidewire channel portion and a proximal guidewire channel portion, which in this case are formed as parts of a single channel. These portions of the guidewire channel can be used as separate channels, because of the incorporation of the rupturable membrane. Use and construction of such catheters are fully disclosed in the drawings and specification of the aforementioned patent applications, upon which this application is based, and which are incorporated herein for reference.

A centering balloon 22 in the form of a coil is attached to the catheter body 12 at a plurality of attachment points 32 spaced along both sides of the catheter body 12. The attachment points 32 are surface attachments, such as by solvent bonding or ultrasonic welding, and they do not establish flow communication between the balloon coil 22 and the inner lumen 14. The centering balloon coil 22 is shown in the inflated condition. When the balloon coil 22 is deflated for insertion or withdrawal, it lies essentially flat against the catheter body 12. When inflated, the balloon coil 22 assumes a lobed shape drawn inwardly as shown at points 34, adjacent to the attachment points 32. This creates two extremities or lobes 36, 38 for each loop of the balloon coil 22. Any number of lobes could be used, depending upon the intended use of the assembly 10. The lobes 36, 38 are extended equal distances, when inflated, from the catheter body 12 to radially center the catheter body 12, and hence the irradiation ribbon 16, within a blood vessel. If desired to position the radioactive material closer to one side of the blood vessel, a balloon coil 22 can have only one lobe per loop, or one lobe 36 can be made longer than the opposing lobe 38. Similarly, each loop of the balloon coil 22 is shown to have identical lobes 36, 38 to ensure that the catheter body 12 is held parallel to the walls of the blood vessel. If desired to angle the catheter body along the blood vessel to tailor the radiation exposure to a particular stenotic segment, adjacent loops of the balloon coil 22 could be formed with different sized lobes without departing from the spirit of the invention.

The balloon coil 22 is shown attached in flow communication at its distal end 26 and at its proximal end 28 to the inflation lumen 40 inside the inflation channel 24. A single flow connection anywhere along the balloon coil 22 could be used, if desired. The inflation channel 24 is shown formed as a duct on the wall of the catheter body 12, but it could be formed inside the inner lumen 14 or the inflation lumen 40 could be formed through the catheter wall. The inflation lumen 40 has an inlet 30 where the inflation fluid is introduced.

FIGS. 3 and 4 show another embodiment of the catheter assembly 10' of the present invention, with a catheter body 12', a guidewire channel 18, and an inflation channel 24' much like the first embodiment. The principal difference between the embodiments is that the radial positioning or centering balloon is formed as a plurality of essentially annular balloon rings 42. Each balloon ring 42 has two extremities or lobes 44, 46, which function essentially the same as the lobes 36, 38 on the balloon coil 22 of the first embodiment. Each balloon ring 42 is attached in flow communication to the inflation lumen 40' at a plurality of attachment points 32' spaced along the inflation channel 24'. Flow communication between the interior of the balloon ring 42 and the inflation lumen 40' is by means of a plurality of inflation ports 48 located at the attachment points 32'. Other forms of the positioning balloon in addition to the two shown here could be devised without departing from the present invention.

Yet another embodiment of the present invention is shown as catheter assembly 10" in FIGS. 5, 6, and 7. A plurality of flexible wire loops 50 are arranged adjacent to the portion of the catheter body 12" where the irradiation source will be located. As seen in FIG. 5, the wire loops 50 are in a contracted condition, with distal ends 54 fixedly attached to the catheter body 12", and with proximal ends 56 free to move relative to the catheter body 12". Each free end 56 is attached to a relatively stiff expansion wire 52, with the plurality of expansion wires 52 passing through an expansion wire guide channel 58 formed on the catheter body 12". The catheter assembly 10" also has a guidewire channel 18, like the first two embodiments. The guidewire is not shown in FIG. 5, for the sake of clarity.

In FIG. 6, the wire loops 50 have been expanded by pushing distally on the expansion wires 52, thereby pushing the free ends 56 of the wire loops 50 toward the attached ends 54. Selective expansion of the wire loops 50 in this way radially positions or centers the catheter body 12" within the blood vessel. Alternatively, the wire loops 50 could have their free ends located near the distal end of the catheter body with the attached ends located proximally, and pulling on the expansion wires could pull the free ends toward the attached ends to expand the wire loops. Further, self-expanding wire loops could be used, with expansion occurring upon withdrawal of a restraining sheath. All of these alternatives are in accordance with the spirit of the present invention.

OPERATION

Irradiation could be accomplished either before or after the performance of the angioplasty procedure. In either case, a guidewire 20 will be in place, inserted to the site of the stenosis. If an angioplasty balloon catheter is in place, it can be withdrawn from the guide catheter, leaving the guidewire 20 in place. The proximal end of the guidewire 20 is inserted into the distal end of the guidewire channel 18 on the catheter assembly 10, 10', 10" of the present invention. The catheter body 12 is then inserted to the site of the stenosis, over the guidewire 20. The irradiation ribbon 16 can be in place within the catheter body 12 prior to insertion, or it can be inserted into the catheter body 12 after the catheter body 12 is in place. If the embodiment in use incorporates the proximal guidewire channel 19 or the full length channel with the rupturable membrane, the guide catheter O-ring can be tightened sealingly around the proximal end of the catheter body 12 to facilitate the injection of dye while allowing free guidewire movement. This aids in visualization of the radiation source for positioning purposes. Furthermore, use of the proximal guidewire channel 19 or the full length channel permits free movement of the guidewire relative to the catheter body as described earlier. When the radioactive seeds are in place within the dilated area of the blood vessel, inflation fluid is introduced into the inflation lumen 40 and pressurized to inflate the positioning balloon, such as the balloon coil 22 or the balloon rings 42, thereby radially positioning or centering the catheter body 12 within the blood vessel. Alternatively, the positioning balloon can be inflated first, followed by insertion of the irradiation ribbon. If the wire loop positioning means are used, of course, the expansion wires 52 could be used to expand the wire loops 50.

Instead of using the positioning balloon or the wire loops, it may be desired to use the bent guidewire method of radially positioning the distal end of the catheter body. If the physician observes that the distal end of the catheter body 12, where the irradiation seeds are located, is not positioned radially as desired, the guidewire 20 is first rotated to orient a bend near the distal end of the guidewire 20 as desired. The bend can be a relatively gentle bend as shown in FIGS. 1 or 3, or it can be more pronounced, depending upon the physical configuration of the blood vessel and the stenosis being treated. Further, a series of bends might be appropriate. The bends could be introduced into the guidewire 20 prior to original insertion of the guidewire 20, or the guidewire 20 can be withdrawn, bent appropriately, and reinserted, if the catheter in use has a full length guidewire channel. After rotation of the guidewire 20 to orient the bend in the direction of desired deflection of the catheter body 12, the catheter body 12 is held in place longitudinally while the distal end of the guidewire 20 is carefully withdrawn into the distal end of the guidewire channel 18. As the bend on the distal end of the guidewire 20 enters, or begins to enter, the distal end of the guidewire channel 18, the guidewire 20 exerts a transverse force on the wall of the guidewire channel 18. This transverse force is in turn transferred to the distal end of the catheter body 12, causing it to deflect in the desired direction.

Regardless of the method used to radially position the irradiation source, the source is then left in place until the desired dose has been administered. After leaving the radiation source in place for the desired length of time to achieve the desired radiation dose, the catheter assembly 10 can be withdrawn, leaving the guidewire 20 in place for insertion of an angioplasty catheter or for the accomplishment of other procedures as required.

While the particular Irradiation Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An irradiation catheter assembly for disposing a nuclear irradiation source at a selected position in a blood vessel, comprising:
   a flexible tubular catheter body having an inner lumen;
   an elongated irradiation ribbon disposed within said lumen;
   at least one radioactive element mounted on said ribbon;
   a guidewire channel formed on said catheter body; and
   a guidewire disposed within said guidewire channel for guiding said catheter body to a selected site within the blood vessel.

2. An irradiation catheter assembly as claimed in claim 1, further comprising an expandable wire structure mounted on said catheter body, for radially positioning said radioactive element.

3. An irradiation catheter assembly as claimed in claim 2, wherein said expandable wire structure comprises:
   a plurality of flexible wire loops, each of said wire loops having a first end attached to said catheter body;
   flexing means attached to a second end of each of said wire loops, said flexing means being selectively movable by a user to move said second ends of said wire loops toward said first ends to flex said wire loops radially outwardly, thereby positioning said radioactive element as desired relative to the walls of the blood vessel.

4. An irradiation catheter assembly as claimed in claim 1, wherein a portion of said guidewire channel is formed near a distal end of said catheter body to enable use of said catheter body as a rapid exchange catheter, and further comprising a second guidewire channel portion formed near a proximal end of said catheter body to provide a sealing surface around the perimeter of said body for encircling said guidewire.

5. An irradiation catheter assembly as claimed in claim 1, further comprising:
   at least one balloon mounted on said catheter body, said balloon being inflatable to radially extend at least one extremity of said balloon from said catheter body to position said radioactive element as desired relative to the walls of the blood vessel; and
   an inflation lumen formed on said catheter body, said inflation lumen being connected in flow communication with said balloon for providing inflation pressure to said balloon.

6. An irradiation catheter assembly for disposing a nuclear irradiation source at a selected position in a blood vessel, comprising:
   a flexible tubular catheter body having an inner lumen;
   an elongated irradiation ribbon disposed within said lumen;
   at least one radioactive element disposed near a distal end of said ribbon;
   a guidewire channel formed adjacent a distal end of said catheter body;
   a guidewire disposed within said guidewire channel for guiding said catheter body to a selected site within the blood vessel;
   a closed distal end formed on said inner lumen to retain said radioactive element within said lumen; and
   an expandable centering means mounted on said catheter body adjacent said radioactive element, for selectively centering said catheter body radially within the blood vessel.

7. An irradiation catheter assembly as claimed in claim 6, wherein said centering means comprises an expandable wire structure.

8. An irradiation catheter assembly as claimed in claim 7, wherein said expandable wire structure comprises:
   a plurality of flexible wire loops, each of said wire loops having a first end attached to said catheter body;
   flexing means attached to a second end of each of said wire loops, said flexing means being selectively movable by a user to move said second ends of said wire loops toward said first ends to flex said wire loops radially outwardly, thereby centering said body relative to the walls of the blood vessel.

9. An irradiation catheter assembly as claimed in claim 6, wherein said centering means comprises:
   at least one balloon mounted on said catheter body, said balloon being selectively inflatable to radially extend at least one extremity of said balloon from said catheter body to radially center said catheter body relative to the walls of the blood vessel; and
   an inflation lumen formed on said catheter body, said inflation lumen being connected in flow communication with said balloon for providing inflation pressure to said balloon.

10. A catheter for disposing a nuclear irradiation source at a selected position in a blood vessel over a guidewire, said catheter comprising:
    a flexible tubular body having an inner lumen for receiving the irradiation source;
    a guidewire channel formed on said body for receiving the guidewire;

a positioning means mounted on said body adjacent the intended position of the irradiation source, for positioning said body radially as desired within the blood vessel; and a closed distal end formed on said inner lumen to retain the irradiation source within said lumen;

wherein said positioning means comprises:

at least one balloon mounted on said body, said balloon being inflatable to radially extend at least one extremity of said balloon from said body to position said body as desired relative to the walls of the blood vessel; and an inflation lumen formed on said body, said inflation lumen being connected in flow communication with said balloon for providing inflation pressure to said balloon;

wherein said at least one balloon comprises an inflatable coil surrounding said body.

11. A catheter as claimed in claim 10, wherein said inflatable coil comprises a plurality of loops having a substantially constant diameter.

12. A catheter for disposing a nuclear irradiation source at a selected position in a blood vessel over a guidewire, said catheter comprising;

a flexible tubular body having an inner lumen for receiving the irradiation source;

a guidewire channel formed on said body for receiving the guidewire;

a positioning means mounted on said body adjacent the intended position of the irradiation source, for positioning said body radially as desired within the blood vessel; and a closed distal end formed on said inner lumen to retain the irradiation source within said lumen;

wherein said positioning means comprises:

at least one balloon mounted on said body, said balloon being inflatable to radially extend at least one extremity of said balloon from said body to position said body as desired relative to the walls of the blood vessel; and an inflation lumen formed on said body, said inflation lumen being connected in flow communication with said balloon for providing inflation pressure to said balloon;

wherein said at least one balloon comprises at least one substantially annular balloon surrounding said body.

13. A catheter as claimed in claim 12, further comprising a plurality of substantially annular balloons surrounding said body, said plurality of substantially annular balloons having extremities extending radially from said body by substantially equal distances.

14. A catheter as claimed in claim 13, wherein each of said substantially annular balloons comprises a plurality of lobes extending substantially equidistantly from said body.

15. A method for irradiating a stenotic segment of a blood vessel, said blood vessel having a guidewire disposed therein, said method comprising the steps of:

providing an irradiation catheter having a closed distal end and having a guidewire channel formed adjacent said distal end;

providing an irradiation ribbon having a radioactive source adjacent its distal end;

inserting a proximal end of said guidewire through said guidewire channel;

inserting said irradiation catheter into said blood vessel over said guidewire, until said distal end of said irradiation catheter is located within said stenotic segment;

inserting said irradiation ribbon into said irradiation catheter, until said radioactive source is located within said stenotic segment.

16. A method as claimed in claim 15, further comprising the step of selectively positioning said distal end of said irradiation catheter at a desired radial position relative to the wall of said blood vessel.

17. A method as claimed in claim 16, wherein said step of selectively positioning said distal end of said irradiation catheter comprises the steps of:

providing an expandable positioning means on said irradiation catheter, near said distal end of said catheter; and selectively expanding said positioning means to radially position said irradiation catheter as desired.

18. A method as claimed in claim 17, wherein:

said expandable positioning means comprises a wire structure; and said step of expanding said positioning means comprises the step of expanding said wire structure.

19. A method as claimed in claim 17, wherein:

said expandable positioning means comprises an inflatable structure; and said step of expanding said positioning means comprises the step of inflating said inflatable structure.

20. A method as claimed in claim 16, wherein said step of selectively positioning said distal end of said irradiation catheter comprises the steps of:

introducing a bend into said guidewire near a distal end of said guidewire;

rotating said guidewire to orient said bend toward a direction of desired deflection of said irradiation catheter; and partially withdrawing said guidewire from said guidewire channel while holding said irradiation catheter in place longitudinally, until said bend exerts sufficient force on said guidewire channel to cause said irradiation catheter to deflect in said desired direction by a desired amount.

* * * * *